United States Patent [19]

Naruse et al.

[11] Patent Number: 5,041,607

[45] Date of Patent: Aug. 20, 1991

[54] PROCESS FOR CRYSTALLIZING L-ALPHA-ASPARTYL-L-PHENYL-ALANINE METHYL

[75] Inventors: Masayoshi Naruse, Yokohama; Haruo Kawasaki, Tokyo; Shinichi Kishimoto, Yokkaichi; Harutoshi Oura, Kawasaki; Masao Nakamura, Yokohama; Hideo Takeda, Inagi, all of Japan

[73] Assignee: Ajinomoto Co., Inc., Tokyo, Japan

[21] Appl. No.: 293,565

[22] Filed: Jan. 3, 1989

Related U.S. Application Data

[60] Continuation of Ser. No. 54,494, May 27, 1987, abandoned, which is a division of Ser. No. 839,819, Mar. 12, 1986, abandoned, which is a continuation of Ser. No. 482,542, Apr. 6, 1983, abandoned.

[30] Foreign Application Priority Data

Apr. 12, 1982 [JP] Japan .................................. 57-60671

[51] Int. Cl.$^5$ .......................................... C07C 224/00
[52] U.S. Cl. ....................................................... 560/41
[58] Field of Search ............................................ 560/41

[56] References Cited

FOREIGN PATENT DOCUMENTS 91787 10/1983 European Pat. Off. .
167268 12/1980 Japan ..................................... 560/41

*Primary Examiner*—Bruce Gray
*Attorney, Agent, or Firm*—Oblon, Spivak, McClelland, Maier & Neustadt

[57] ABSTRACT

A crystalline L-alpha-aspartyl-L-phenyl-alanine methyl ester product is disclosed. The product is obtained by crystallizing the ester from an aqueous solution, by cooling. The initial concentration of ester in the aqueous solution used provides at least 10 grams of precipitated solid phase per liter of solution. The solution is cooled through conductive heat transfer without effecting forced flow to form a sherbet-like pseudo solid phase.

14 Claims, 13 Drawing Sheets

PROCESS FOR CRYSTALLIZING L-ALPHA-ASPARTYL-L-PHENYL-ALANINE METHYL

This application is a continuation of application Ser. No. 07/054,494, filed on May 27, 1987, now abandoned, which is a division of application Ser. No. 06/839,819, filed 3/12/86, now abandoned, which is a continuation of application Ser. No. 06/482,542, filed 4/6/83, now abandoned.

DETAILED DESCRIPTION OF THE INVENTION

This invention relates to a process for crystallizing and separating L-α-aspartyl-L-phenylalanine metyl ester under some specific crystallization conditions.

L-α-aspartyl-L-phenylalanine methyl ester (hereinafter abbreviated as APM) is a substance which is expected to find wide applications as a new low-calorie sweetener due to its good sweetening properties. As processes for industrially producing this APM, the following processes are typical.

That is, there are known a process of binding an N-substituted aspartic acid anhydride with phenylalanine methyl ester in an organic solvent (U.S. Pat. No. 3,786,039), a process of directly binding a strong acid addition salt of aspartic acid anhydride with phenylalanine methyl ester (Japanese Patent Publication No. 14217/74), a process of condensing an N-substituted aspartic acid with phenylalanine methyl ester in the presence of an enzyme and eliminating the substituent (Japanese Patent Publication No. 135595/80), and the like.

In industrial production, a crystallizing step to isolating APM from a reaction solution is necessary for obtaining the final product in any of the processes described above. This crystallizing step is usually conducted, for example, by re-dissolving a crude product in water, a organic solvent or an aqueous organic solvent, cooling the solution through heat exchange with a refrigeration medium (forced cyclization type indirect cooling system) or evaporating part of the solvent under reduce pressure (self-evaporating system) using a crystallizer equipped with a stirring means, and dewatering and filtering out the thus precipitated crystals by means of a centrifugal separator or the like.

However, the thus obtained APM crystals are fine needle-like crystals, and therefore show extremely bad solid-liquid separability in filtration and dewatering procedure. Thus the above-described processes have practical problems.

To illustrate one case, when 600 liters of a slurry containing APM crystals obtained by one of the above-described processes (see Comparative Example) was subjected to solid-liquid separation by filtering for 2 hours and dehydrating for one hour in a centrifugal separator having a diameter of 36 inches and a volume of 92 liters (number of revolutions: 1,100 r.p.m.; centrifuging effect: 600 G), the resulting cake had a water content of 45 to 50% or more. The water content as used herein is defined as (water amount in the cake/whole amount of wet cake) × 100%.

In addition, there is found another defect that, when a series of the procedures of scraping this cake and conducting solid-liquid separation of a fresh slurry containing APM crystals are repeated, the base layer of cake between so tightly hardened that its removal requires much labor and time.

Further, in a drying step following the crystallizing step, the drying load is too high due to the high water content of the cake, and the resulting powder has such large bulk specific volume that it is extremely difficult to handle.

Table 1 shows powder properties of APM crystals obtained by the crystallizing process of the present invention (see Example 1) and that obtained by one conventional process (see Comparative Example).

TABLE 1

|  | Conventional Process | Process of the Invention |
|---|---|---|
| Static (loose) specific volume (cc/g) | 6–7 | 3–4 |
| Close (packed) specific volume (cc/g) | 3–4 | 2–3 |
| Rate of dissolution (min.) | 14–17 | 5–6 | in crystallizing other materials, it has been known that the above-described problems in the crystallizing procedure can be removed by conducting the crystallization employing a low concentration and a slow cooling rate to obtain crystals having a large diameter. With APM crystals, however, such crystallization procedure results in formation of needle-like crystals growing only in a longitudinal direction, failing to provide expected effects. For example, when seed crystals were added to a 0.8 wt % APM solution and the solution temperature was decreased from 15° C. to 5° C. in two days, crystals grew 214% in the length direction but only 15% in the diameter direction.

As a result of intensive investigations to improve workability of the aforesaid step in the production of APM by examining various conditions, the inventors have found the following novel facts.

That is, surprisingly, it has been found that, in crystallizing APM from its solution of a certain concentration or above by cooling without stirring, APM crystals take up the solvent into the space formed among them, and the whole solution thus appears apparently solidified, and that the crystals obtained in this state show extremely good properties in subsequent solid-liquid separation procedure. Observation of the crystals under a scanning type electromicroscope revealed that several needle-like crystals are bundled to form apparently one crystal (to be described hereinafter).

The bundle-like crystal aggregates of the present invention are extremely strong against physical impact as long as they are not under growing in a supersaturated solution, and have been confirmed to maintain 5- to 10-fold or more diameter as compared to that of conventional crystals even after being transported, separated or dried.

More surprisingly, even under such crystallizing condition in which, with ordinary substances, crystals fixedly deposit on a heat-transferring surface to cause so-called scaling which is difficultly removable, precipitation of APM crystals in accordance with the present invention is found to allow complete removal of the crystal layer from the cooling surface.

As a result of intensive investigations to apply the above-described findings to an actual process, the inventors have achieved remarkable improvement in workability in the step of precipitating APM crystals from an APM solution by cooling the solution under the condition of forming a pseudo solid phase to obtain crystals showing good separability, thus having completed a novel crystallizing process providing industrially great economical effects. As a result of further investigations, the inventors have found that, once the solution takes a pseudo solid phase, it can maintain its good separability even when subjected to a desupersaturation procedure of rapid cooling accompanied by causing forced flow, which serves to increase the efficiency of the step and improve crystallization yield, thus having completed the present invention.

That is, a characteristic aspect of the present invention is to obtain bundled, large-diameter APM crystal aggregates by cooling as fast as possible an APM aqueous solution employing such crystallizing conditions or crystallizers that natural heat transfer by convection is realized only in the very early stage of the crystallizing step, then heat transfer is controlled by conduction. According to the present invention, solid-liquid separability and powder properties of the product can be improved, workability in each step being remarkably improved. Therefore, the present invention provides an APM-crystallizing process which is economically quite advantageous. Additionally, due to the above-described properties of the present invention, APM crystals having bad crystal habit can be converted to APM crystals having good crystal habit by the recrystallization process in accordance with the present invention, and APM containing impurities such as diketopiperazine (DKP), an cyclized product of APM, and L-α-aspartyl-L-phenylalanine can be freed of the impurities by subjecting the impurities-containing APM to the crystallizing process of the present invention coupled with a decrease in the amount of adhering mother liquid in a solid-liquid separation and improvement in cake washability.

The present invention will now be described in more detail below.

In the process of the present invention, cooling is conducted without forced flow caused, for example, by mechanical stirring. Additionally, it is desirable to render the whole solution into a sherbet-like pseudo solid phase to finish natural flow phenomenon resulting from temperature distribution as fast as possible. For the purpose of comparison, electronmicroscopic photographs of bundled crystals obtained by the process of the present invention (FIG. 1A ($\times 58$), and FIG. 1B ($\times 580$)), fine crystals obtained by indirect cooling under forced flow, one of the conventional processes (FIG. 2A ($\times 560$) and FIG. 2B ($\times 1280$)), and dendrite crystals obtained without causing forced flow and under such condition that no sherbet is formed (FIG. 3A ($\times 51$) and FIG. 3B ($\times 350$)). From these photographs, it can be easily understood that the three crystals, which show the same results in X-ray powder diffractiometry, are clearly different from each other in shape and size due to the difference in crystallizing manner.

As a crystallizer for satisfying the above-described procedure conditions, FIG. 4 shows an example of continuous crystallizers, in which a jacketed U-tube having nozzles on both ends is used. Upon initiation of the crystallizing procedure, a feed solution is previously charged in the tube before initiation of cooling. At a stage where crystallization has proceeded in the tube, feed solution is pressed into the tube through feed inlet 1 at a slow rate, upon which a sherbet-like slurry is pressed out of the tube through opposite outlet 2. The sherbet-like slurry can be continuously obtained onward by cooling through heat transfer by conduction and feeding the solution in such flow rate that enough residence time for crystallization to be completed is attained.

Additionally, the crystallizer may not necessarily ba a U-tube, and a vertical or horizontal straight tube and any curved tube that does not suffer pressure loss more than is necessary may be employed as well.

FIG. 5 shows an example of batchwise crystallizers. Feed solution is introduced through feed inlet 1. After completion of charging the solution, a refrigeration medium is introduced into cooling plates 2 or cooling tube and jacket 3 to cool the contents. After a predetermined period of time, discharge valve 4 is opened to discharge a sherbet-like slurry.

FIGS. 6 and 7 show examples of conducting the process of the present invention using a conventional apparatus. Procedures are continuous in both cases.

In FIG. 6, a rotating steel belt is used as a cooling surface (the belt being cooled, for example, by blowing a refrigeration medium to the back of the belt), and a feed solution is continuously introduced onto the belt to crystallize. The formed sherbet-like slurry is recovered by scraping with scraper 1 provided on the other end. In this embodiment, for the purpose of forming a thick sherbet layer on the belt, guides 2 may be provided on the sides of the belt, or a frame may be fixedly provided on the belt to thereby prevent the solution from flowing over before solidifying. In some cases, semi-continuous procedure may be employed.

FIG. 7 shows an embodiment of utilizing an evaporate-condenser. A feed solution is introduced to the center 3 of two contact-rotating drums 1 rotating outward. The drums are cooled from inside with a refrigeration medium instead of being heated from inside with steam, on which sherbet deposits as a result of crystallization. The thus formed sherbet is scraped by scraper 2.

These embodiments are particularly designed or intended for satisfying the aforesaid special conditions of the crystallization to be employed in the process of the present invention. The inventors do not know that the above-described apparatuses have been used for crystallizing APM as well as other materials through heat transfer by conduction. Processes for crystallizing APM with the use of any other apparatuses which satisfy the specific crystallization conditions of this invention are of course within the scope of this invention.

To attain an apparantly solidified state, the solution must contain about 10 g or more solids per liter of the solvent at that point. That is, in an aqueous solution system, satisfactory recovery of APM can be attained by cooling the system to 5° C., taking the solubility of APM into consideration. Theoretically, an initial concentration of the APM solution before crystallization of 1.5 wt % suffices since the saturation concentration at the temperature is 0.5%. However, in a low supersaturated region, crystallizing rate is too slow. Therefore, practically the aqueous system must contain about 2 wt % or more APM for forming the sherbet state. In order to obtain crystals having large diameter, solidification must proceed at a faster rate. For this purpose, the initial concentration is desirably about 3 wt % or more.

FIG. 8 shows the results of measuring solubility of APM in water.

On the other hand, the upper limit of the concentration depends upon stability of APM in solution at elevated temperatures and its soluble concentration and, in the aqueous system, a concentration of about 10% or less, which is a saturation concentration of APM at 80° C., is usually a suitable upper limit.

As the crystallizing solvent, water suffices, which may optionally contain other solvents as long as the spirit of the present invention is not spoiled, i.e., no particular troubles take place in the practice of the present invention.

For effectively practicing the process of the present invention, cooling rate is an important procedure factor. However, in the cooling step based on heat transfer by conduction, a temperature distribution appears within a solution being cooled, and the cooling rate is not timewise constant, thus definite control of cooling rate being difficult. However, average temperature of a cooled solution after a given period of time is decided by the temperature of the refrigeration medium used, the initial temperature of the cooled solution, and the maximum distance between the cooled solution and the heat-transfer surface. The initial temperature of the cooled, solution depends upon the aforesaid concentration of APM and, as the refrigeration medium, a known one such as propylene glycol, ethylene glycol or cooling water may be used. The temperature of the refrigeration medium is most suitably −5° C. to 35° C. in view of prevention of freezing of the solvent and time required for cooling. Further, as to the maximum distance between the cooled solution and the heat-transfer surface, the larger the distance, the more the difference in crystallization degree due to greater temperature distribution within the cooled solution. In addition, decomposition of APM proceeds so much that predetermined supersaturation cannot be attained, thus separability being adversely affected to a large degree. Therefore, even the remotest part of the solution being cooling is desirably 500 mm or less from the heat-transfer surface. In any case, those skilled in the art can easily find conditions necessary for rendering the whole solution into a pseudo solid phase in the illustrated crystallizers, which are the marrow of the present invention, through simple preliminary experiments.

The thus obtained sherbet-like pseudo solid phase comprising APM crystals and the solvent does not itself show any fluidity, but shows extremely good separating properties from the cooling surface, thus causing no troubles upon discharge out of the crystallizer. It can be easily destroyed into a slurry, for example, by stirring and can be transported through pumps or the like.

Additionally, in the process of the present invention, cooling of the system is conducted through heat transfer by conduction, and hence it requires a longer time to cool to a desired temperature than that in cooling under forces flow. Needless to say, the process of the present invention provides more advantages than compensate for the disadvantage. However, in order to more raise efficiency and improve yield, it is possible to conduct desupersaturating procedure subsequent to the aforesaid crystallizing step.

That is, the sherbet-like pseudo solid phase obtained by crystallization through heat transfer by conduction and comprising APM crystals and the solvent is rapidly cooled subsequent to destruction of the solid phase, for example, by stirring to thereby remove residual supersaturation in a short time. However, where the proportion of APM crystals additionally precipitated in the desupersaturating procedure accounts for about 25% or more the whole solid phase APM finally obtained, solid-liquid separability of the slurry is sharply deteriorated. Therefore, the desupersaturation to be carried out is desirably controlled to less than the above-described degree.

The present invention will now be described in more detail by the following non-limiting examples of preferred embodiments of the present invention.

EXAMPLE 1

This example was conducted using an apparatus shown in FIG. 9.

380 Liters of a feed solution containing dissolved therein 17.7 Kg of APM (containing 3% DKP) (55° C.; initial concentration of APM: 4.4 wt %) was charged in a stainless steel crystallizer having a diameter of 400 mm (maximum distance between the cooled solution and the cooling surface: 75 mm) and having jacket 3 and inner cooling plates 2, and a 0° C. refrigeration medium was circulated through the jacket and the cooling plates to conduct cooling for 3 hours, during which cooling through heat transfer by conduction became predominant about 15 minutes after initiation of the cooling. The whole solution became a pseudo solid phase after about one hour.

Thereafter, the contents were discharged into tank 7 equipped with cooling coil 5 and stirrer 6 to destroy the solid phase. On this occasion, the average temperature of the slurry was about 16° C., and the APM concentration of the mother liquid was 0.9 wt %. Then, a refrigeration medium was introduced into the coil under further stirring to conduct cooling for one hour to thereby lower the temperature of the slurry to about 7° C. The APM concentration of the mother liquor was 0.7 wt %.

When the thus obtained slurry was filtered and dewatered using a centrifugal separator 8 having a diameter of 36 inches, water content of the cake decreased to 25% after only 20 minutes. Yield: 19 Kg (wet); recovery ratio: 86%; DKP content: 0.1%.

Additionally, APM crystals additionally precipitated in the desupersaturation procedure accounted for about 5% of the whole solid phase finally obtained.

Similar results were obtained by crystallizing APM using an apparatus having a cooling tube in place of the cooling plate.

With a slurry obtained by a conventional process (see Comparative Example to be described below), the water content was as high as 45 to 50% even after 2-hour filtration and 1-hour dewatering (3 hours altogether).

COMPARATIVE EXAMPLE

This comparative example was conducted using an apparatus shown in FIG. 10. A feed solution was continuously introduced through feed inlet 8. Two stainless steel tanks 4 (volume: 100 liters) equipped with stirrer 1, outer heat-exchanger 2, and jacket 3 were used in series. Stirring speed was 50 r.p.m. APM concentration of the feed solution was 4.4 wt %, and the flow rate was 60 liters/hr. The average temperature in the first tank was 25° C., and that in the second tank 10° C. Additionally, in FIG. 10, numeral 5 designates a receiving tank equipped with stirrer 1 and cooling coil 6, and 7 designated a centrifugal separator.

Results of comparing the process of the present invention with the conventional process with respect to centrifuge-filtration rate and centrifuge dewatering rate are shown in FIG. 11A and FIG. 11B, respectively.

— shows the measured values with APM slurry in accordance with the present invention, and — shows the measured values with APM slurry obtained by the conventional process.

In leaf test by suction filtration to determine specific resistance value, the APM slurry obtained by the process of the present invention showed a specific resistance of $1 \times 10^8$ to $2 \times 10^8$ m/Kg immediately after being discharged and $3 \times 10^8$ to $5 \times 10^8$ m/Kg after desupersaturation, whereas the slurry obtained by the conventional process showed a specific resistance of $5 \times 10^{10}$ to $1 \times 10^{11}$ m/Kg.

EXAMPLE 2

A feed solution having the same composition as in Example 1 was cooled using a steel belt cooler (1.2 m × 5 m; made of stainless steel) as shown in FIG. 12 to crystallize APM. The feed solution was continuously introduced onto the belt through feed inlet 3. Where the feed amount is large, it is preferable to provide guides 2 on the sides of the belt for preventing overflow. In such cases, the guides are not necessarily provided over the full length of the belt, because the solution does not flow out after being rendered sherbet-like.

Cooling was conducted indirectly by jetting 12° C. cooling water on to back of the belt. The solution-feeding rate and the belt speed were adjusted so that the thickness of sherbet, or maximum distance from the cooling surface, became about 10 mm.

The thus obtained sherbet containing APM crystals and water was scraped out by scraper 1 and destroyed in receiving tank 4 by stirring (60 r.p.m.) into a slurry. The average temperature of the product immediately after scraping was about 18° C. Additionally, cooling for desupersaturation was not particularly conducted in the receiving tank.

When about 100 liters of the slurry in the receiving tank was subjected to solid-liquid separation in centrifugal separator 5, the water content of cake was reduced to about 30% after 30 minutes. Yield: 4.3 Kg. The separated mother liquor contained about 1.5 wt % APM. Recovery ratio: 68%.

This steel-belt cooler system has the advantages that, as compared to the system of Example 1, the cooling surface can be smaller due to larger processing speed and that, in view of process flow, the feed solution is not necessarily kept at high temperature because of continuous system, thus decomposition of APM being remarkably reduced.

As is clear from the above descriptions and examples, application of the process of the present invention to crystallization and separation of APM crystals provides the following outstanding advantages from the industrial point view as compared to conventional processes, for example, of forced circulation-outer cooling system or self evaporation system, though energy load required for cooling, etc. is almost the same.

(1) As to solid-liquid separation of a slurry containing APM crystals, a slurry obtained by the conventional process is difficult to reduce in its water content to the degree attained by a slurry obtained by the process of the present invention even when the separation time is prolonged.

(2) In repeatedly conducting the above-described separation procedure, a slurry obtained by the conventional process suffers tight press-solidification of the cake base layer, its removal requiring much labor, whereas a slurry obtained by the process of the present invention does not undergo such a phenomenon. For example, in one embodiment of the process of the present invention, the base layer could be easily removed from the filter surface even after 20 times repeating the procedure, whereas repeated procedure according to the conventional process resulted in tight solidification only after 5 times repeating the procedure, the thus solidified base layer being difficulty removable.

(3) To evaluate the shortening of filtration time and reduction or separation load such as cake removal, realized by applying the process of the present invention, in terms of required filter area, the process of the present invention reduced the area to about 1/10 of less of the area of the conventional process.

(4) Additionally, the remarkable improvement of separability is accomplished by reduction of adhesion of impurity-containing mother liquid onto the crystals to ½ and improvement of washing effect, and hence crude crystallization step may be eliminated by combining cake washing procedure or the like.

(5) Load in a drying step is decreased to about ⅓. For example, drying load necessary for obtaining 100 Kg of dry product powder (water content: 3%) is as follows. With APM crystals containing 50% water and obtained by the conventional process, the load is $5.1 \times 10^4$ Kcal, with neglecting loss in heat transfer procedure, whereas with APM crystals containing 25% water and obtained by the process of the present invention, it is $1.6 \times 10^4$ Kcal.

(6) Dry powder properties are so remarkably improved as shown in Table 1 that handling properties of the powder are improved.

Figure 1A:
FIG. 1A and FIG. 1B are electromicroscopic photographs of APM crystals obtained by the process of the present invention.
Figure 1B:
Figure 2A:
FIG. 2A and FIG. 2B are electronimicrographs of APM crystals obtained by the conventional process.
Figure 2B:
Figure 3A:
FIG. 3A and FIG. 3B are electron microscope photographs of APM crystals obtained without causing forced flow and under such condition that no sherbet is formed.
Figure 3B:
Figure 4:
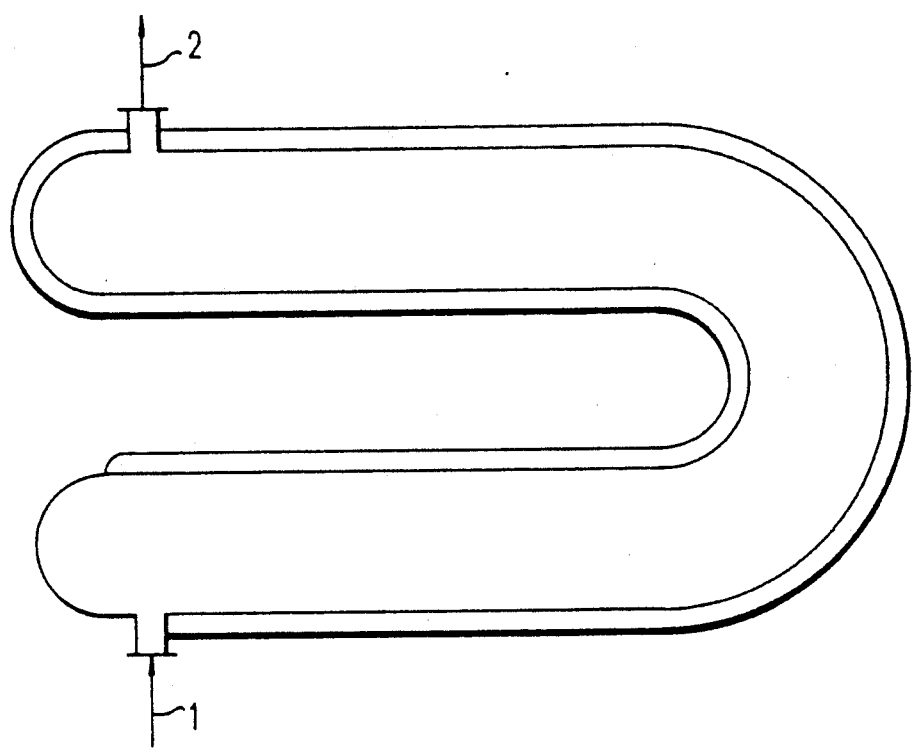
FIGS. 4, 5, 6, and 7 show examples of crystallizers to be used in the present invention.
Figure 5:
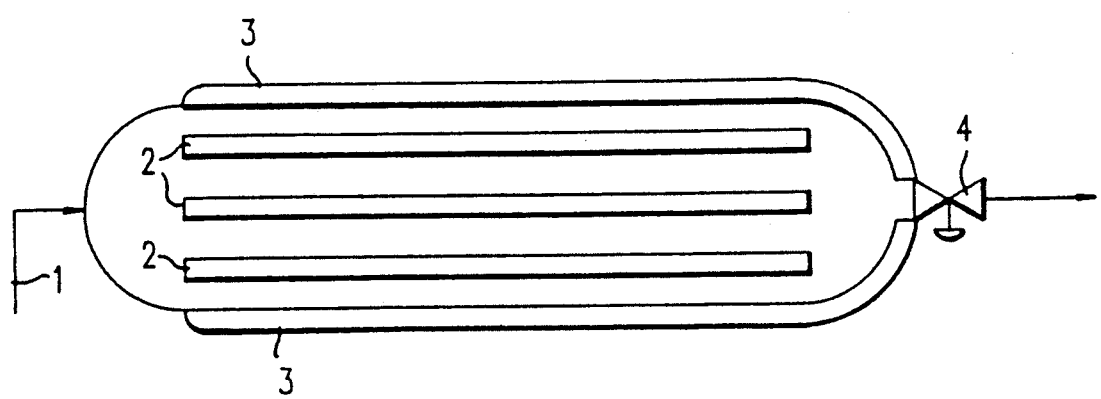
Figure 6:
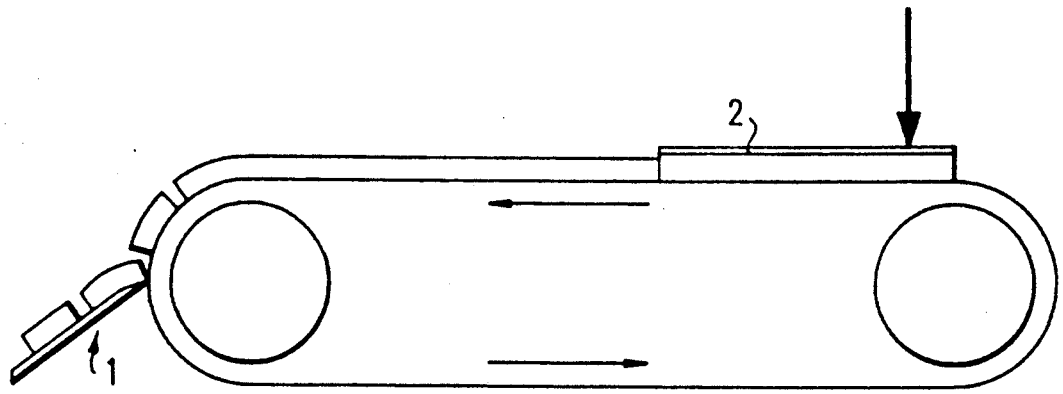
Figure 7:
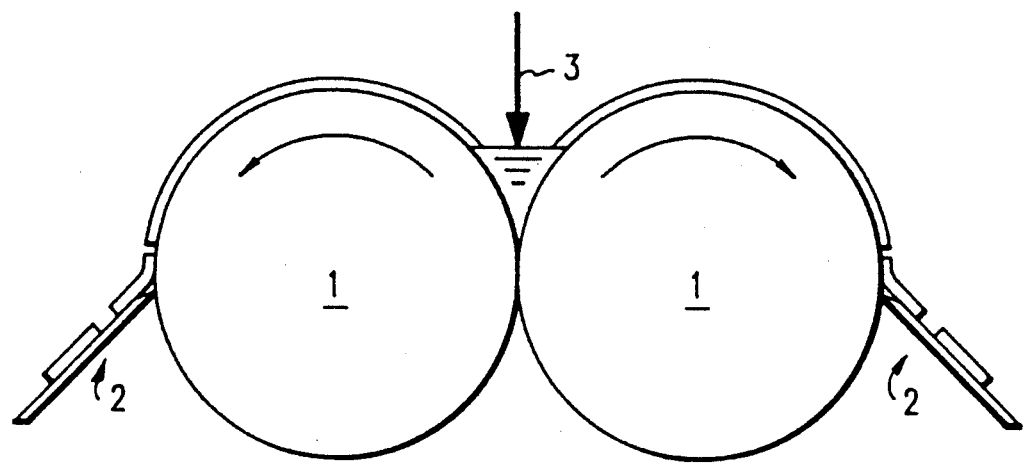
Figure 8:
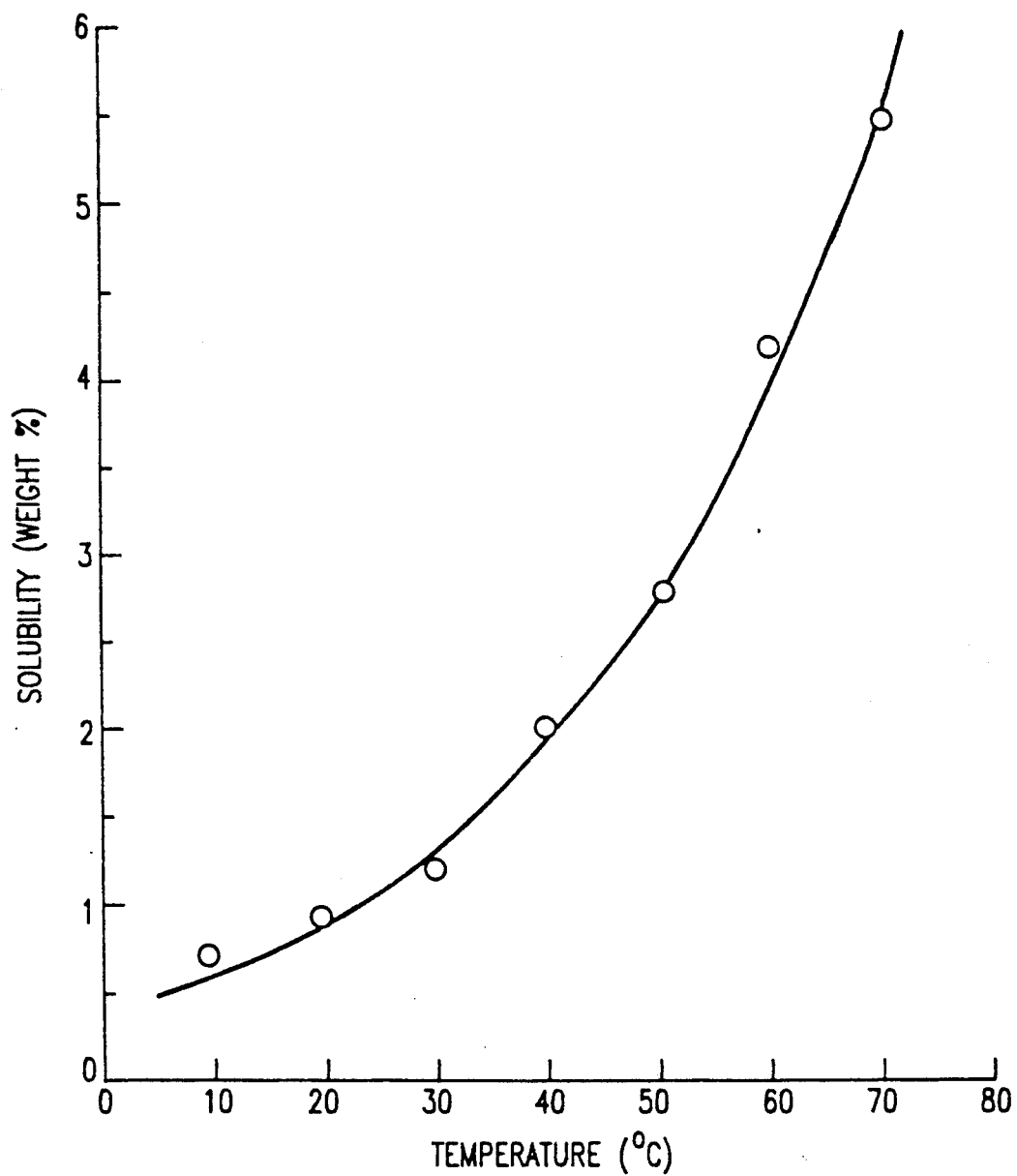
FIG. 8 shows solubility of APM in water.
Figure 9:
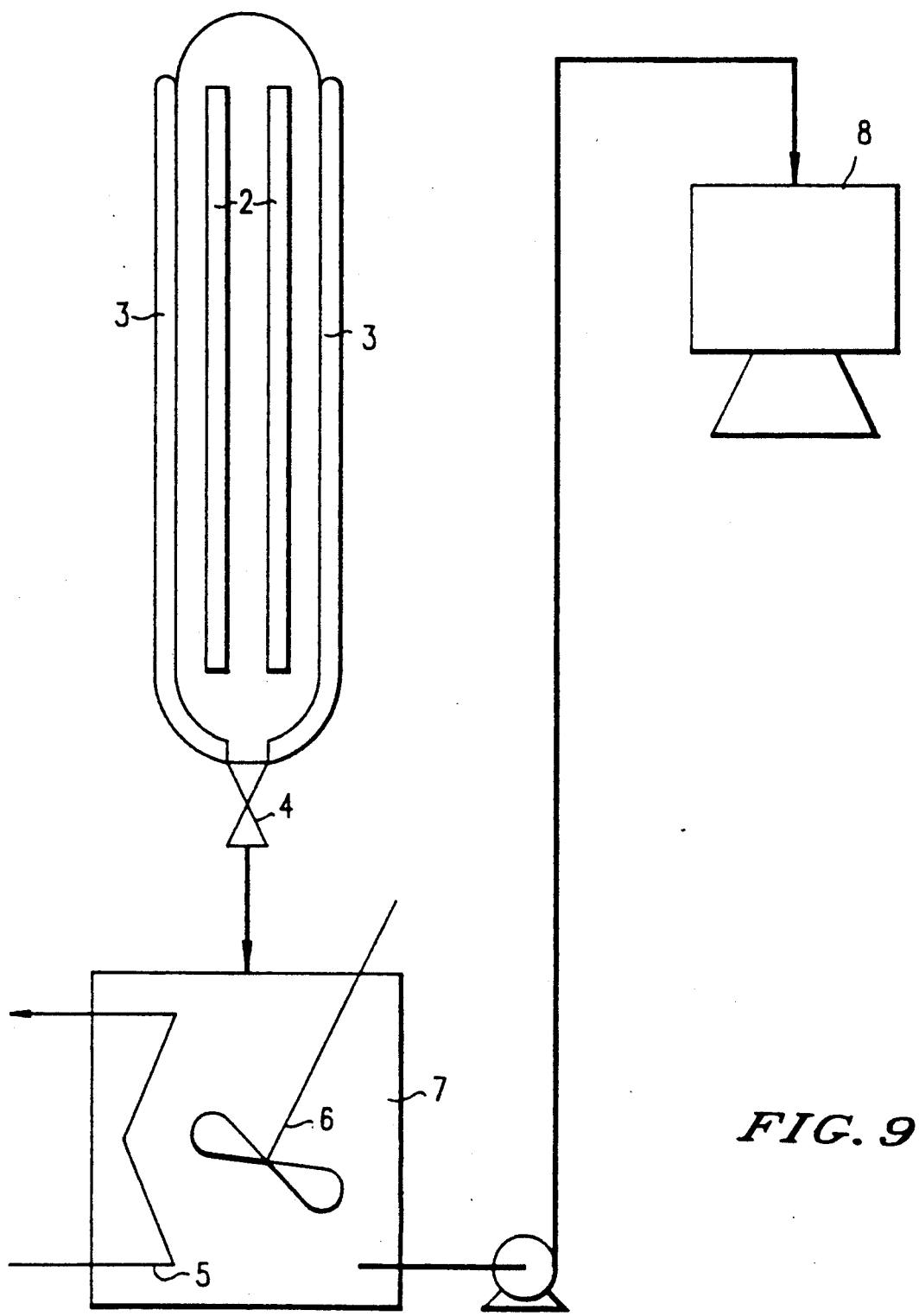
FIG. 9 shows a crystallizer used in Example 1.
Figure 10:
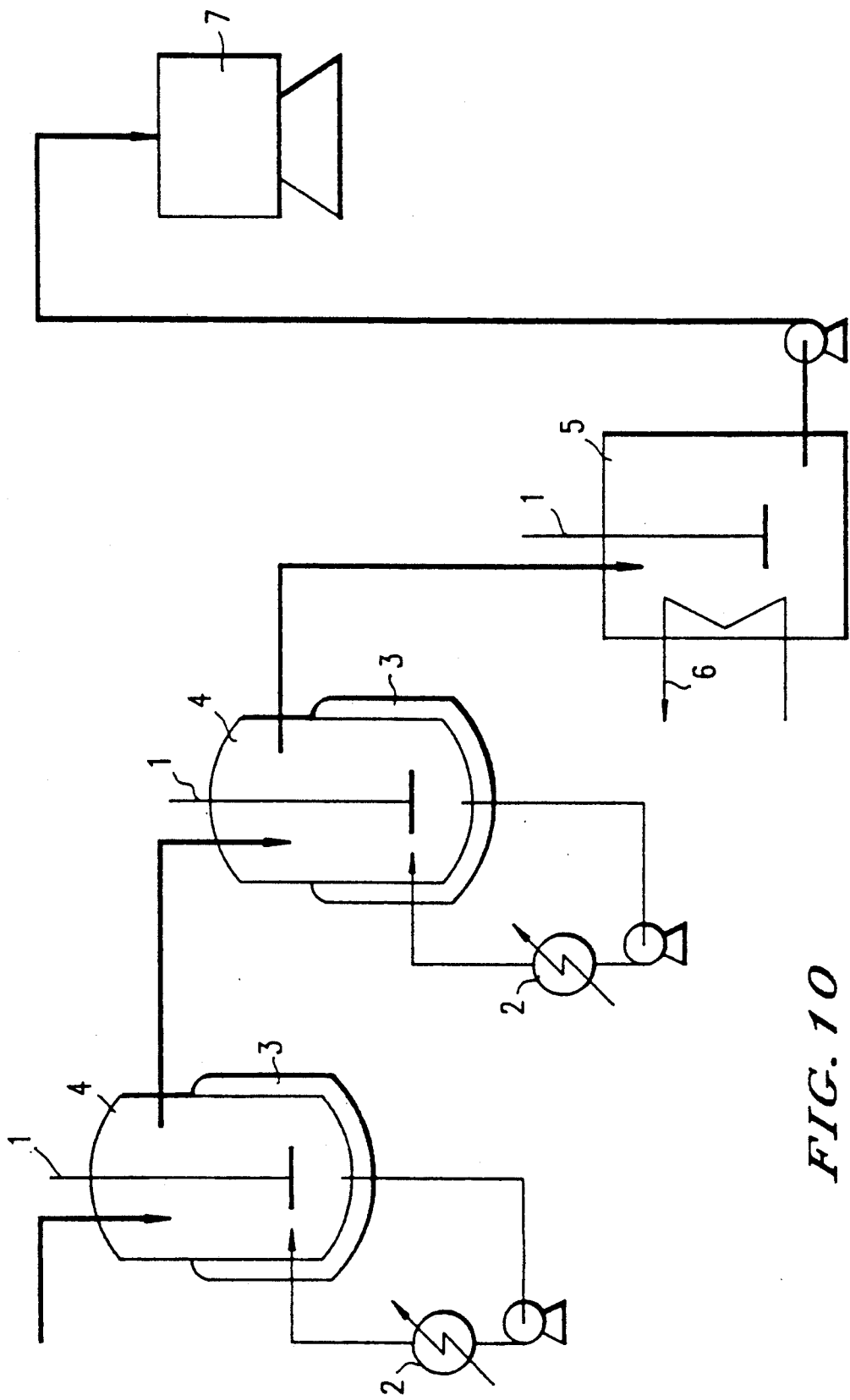
FIG. 10 shows a crystallizer used in conventional process.
Figure 11A:
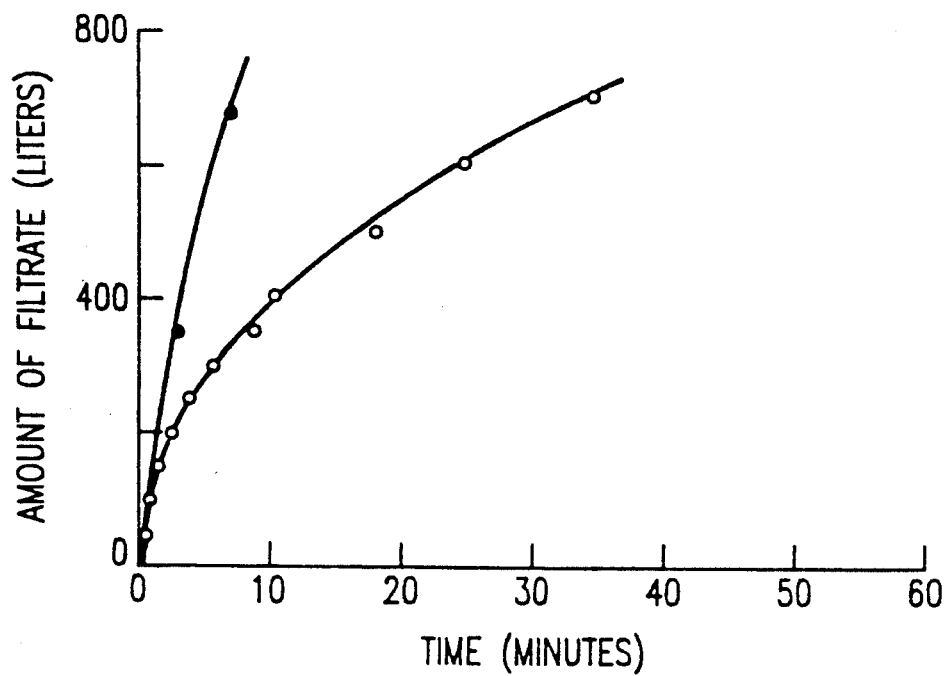
FIG. 11A and FIG. 11B show the results of comparing the process of the present invention with a conventional process with respect to filtration rate and dehydration rate of APM slurry.
Figure 11B:
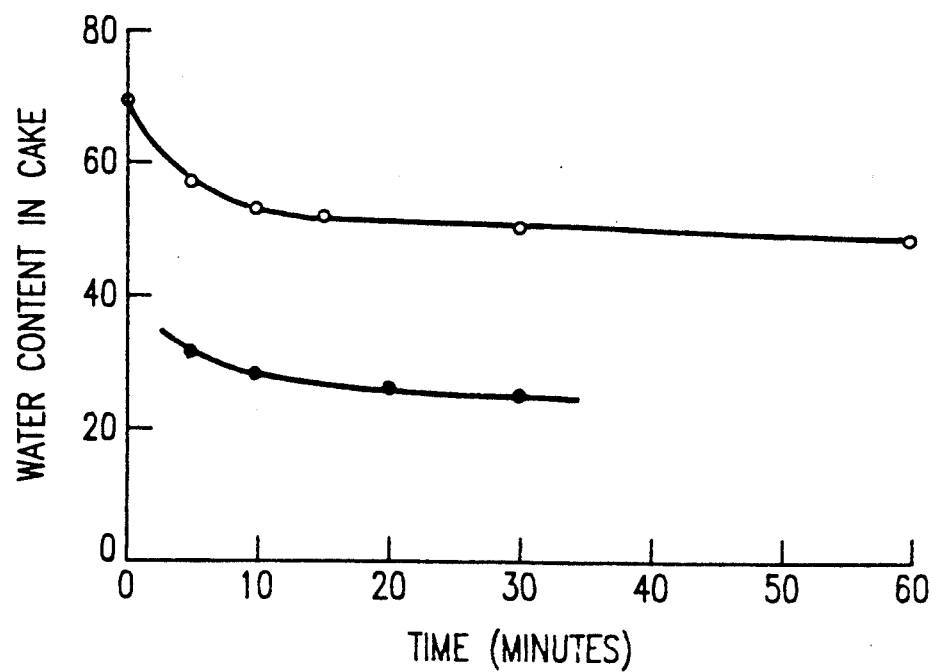
Figure 12:
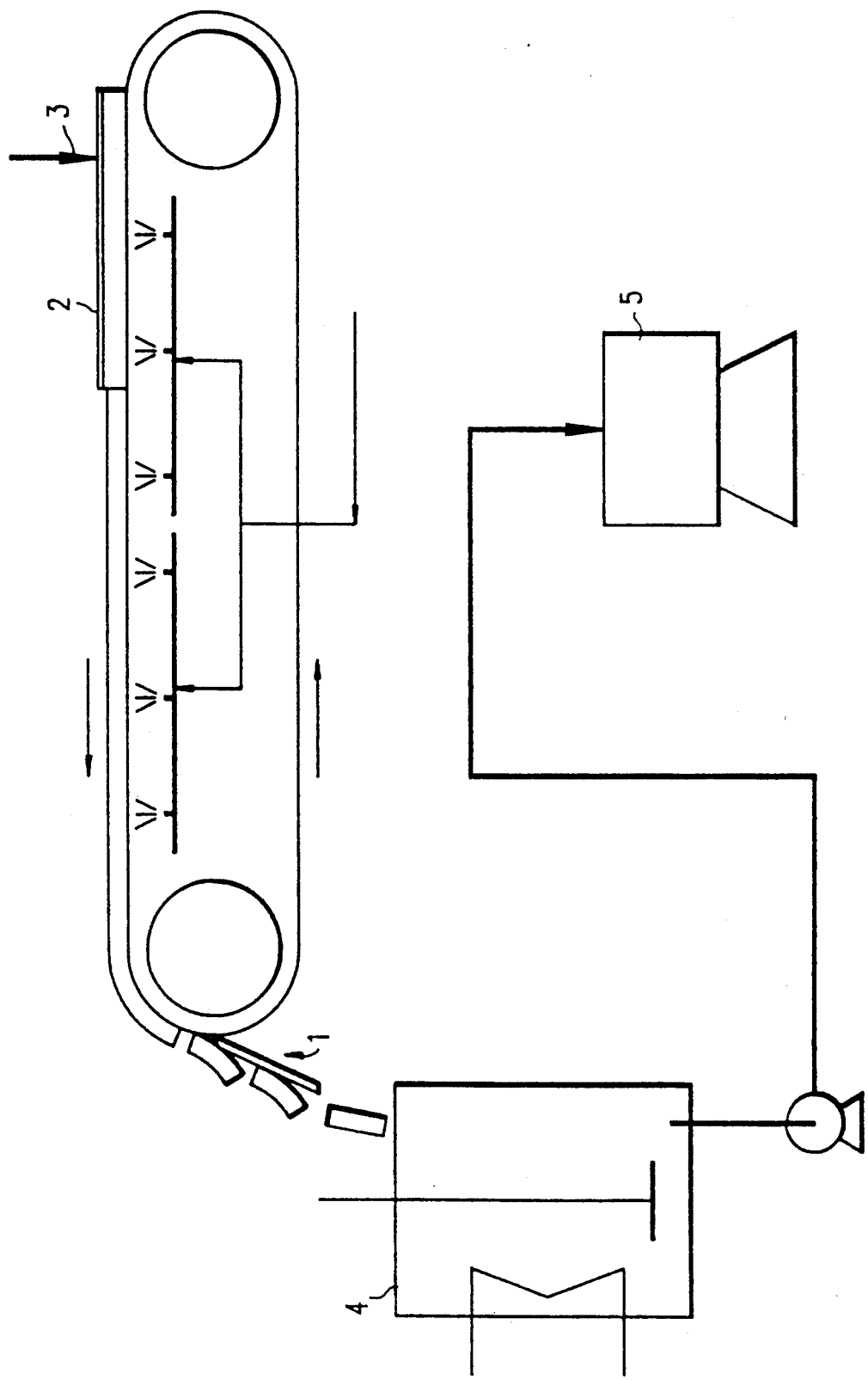
FIG. 12 shows a crystallizer used in Example 2.

What is claimed is:

1. In an industrial-scale crystalline L-alpha-aspartyl-L-phenylalanine methyl ester product obtained by industrial-scale crystallization of L-alpha-aspartyl-L-phenylalanine methyl ester from an aqueous solution of L-alpha-aspartyl-L-phenylalanine methyl ester by cooling, the improvement comprising using a crystallization process comprising the steps of:

(1) preparing an industrial-scale aqueous solution of L-alpha-aspartyl-L-phenylalanine methyl ester, adjusting the initial concentration of the said ester in the solution so that the amount of precipitated solid phase formed after cooling is about 10 grams, or more, per liter of solvent;

(2) charging the solution into a crystallizer equipped with solid cooling surfaces comprising cooling plates or cooling tubes, and a cooling jacket, to cool the aqueous solution without effecting forced flow and by conductive heat transfer, by contacting the solution with the cooling surfaces having a refrigeration medium circulating therein at a temperature of from $-5°$ C. to $+35°$ C. and keeping a distance between the solution and the cooling surface of 500 mm or less to form a sherbet-like pseudo solid phase; and (3) isolating the sherbet-like pseudo solid phase to obtain the industrial-scale crystalline L-alpha-aspartyl-L-phenylalanine methyl ester product, wherein the crystals of said product have a static specific volume of from 3 to 4 cc gram$^{-1}$, a close specific volume of 2 to 3 cc gram$^{-1}$, and a rate of dissolution, in water, of 5 to 6 minutes.

2. The industrial-scale crystalline L-alpha-aspartyl-L-phenylalanine methyl ester of claim 1, wherein the initial concentration of the L-alpha-aspartyl-L-phenylalanine methyl ester in said aqueous solution is from 2 to 10 wt. %.

3. The industrial-scale crystalline L-alpha-aspartyl-L-phenylalanine methyl ester product of claim 1, wherein the initial concentration of the L-alpha-aspartyl-L-phenyl-alanine methyl ester in said aqueous solution is from 3 to 10 wt. %.

4. The industrial-scale crystalline L-alpha-aspartyl-L-phenylalanine methyl ester product of claim 1, wherein said aqueous solution is subjected to a desupersaturation operation carried out by cooling or effecting forced flow, after formation of said pseudo solid phase.

5. The industrial-scale crystalline L-alpha-aspartyl-L-phenylalanine methyl ester product of claim 4, wherein the proportion of L-alpha-aspartyl-L-phenylalanine methyl ester crystals precipitated in the desupersaturation procedure is about 25% or less, based on the total solid phase finally obtained.

6. In a crystalline L-alpha-aspartyl-L-phenylalanine methyl ester product obtained by crystallization of L-alpha-aspartyl-L-phenylalanine methyl ester from an aqueous solution of L-alpha-aspartyl-L-phenylalanine methyl ester by cooling, the improvement comprising using a crystallization process comprising of steps of:

(1) preparing an aqueous solution of L-alpha-aspartyl-L-phenylalanine methyl ester, adjusting the initial concentration of said ester in the solution so that the amount of precipitated solid phase formed after cooling is about 10 grams, or more, per liter of solvent;

(2) charging the solution into a crystallizer equipped with solid cooling surfaces comprising cooling plates or cooling tubes, and a cooling jacket, to cool the aqueous solution without effecting forced flow and by conductive head transfer, by contacting the solution with the cooling surfaces having a refrigeration medium circulating therein at a temperature of from $-5°$ C. to $+35°$ C. and keeping a distance between the solution and the cooling surface of 500 mm or less to form a sherbet-like pseudo solid phase; and (3) isolating the sherbet-like pseudo solid phase to obtain the crystalline L-alpha-aspartyl-L-phenylalanine methyl ester product, wherein the crystals of said product have a static specific volume of from 3 to 4 cc gram$^{-1}$, a close specific volume of 2 to 3 cc gram$^{-1}$, and a rate of dissolution, in water, of 5 to 6 minutes.

7. The crystalline L-alpha-aspartyl-L-phenylalanine methyl ester of claim 6, wherein the initial concentration of the L-alpha-aspartyl-L-phenylalanine methyl ester in said aqueous solution is from 2 to 10 wt. %.

8. The crystalline L-alpha-aspartyl-L-phenylalanine methyl ester product of claim 6, wherein the initial concentration of the L-alpha-aspartyl-L-phenylalanine methyl ester in said aqueous solution is from 3 to 10 wt. %.

9. The crystalline L-alpha-aspartyl-L-phenylalanine methyl ester product of claim 6, wherein said aqueous solution is subjected to a desupersaturation operation carried out by cooling or effecting forced flow, after formation of said pseudo solid phase.

10. The crystalline L-alpha-aspartyl-L-phenylalanine methyl ester product of claim 9, wherein the proportion of L-alpha-aspartyl-L-phenylalanine methyl ester crystals precipitated in the desupersaturation procedure is about 25% or less, based on the total solid phase finally obtained.

11. The industrial-scale crystalline L-alpha-aspartyl-L-phenylalanine methyl ester product of claim 9, wherein said product is dry.

12. The crystalline L-alpha-aspartyl-L-phenylalanine methyl ester product of claim 6, wherein said product is dry.

13. The industrial-scale crystalline L-alpha-aspartyl-L-phenylalanine methyl ester product of claim 1, wherein the initial concentration of the L-alpha-aspartyl-L-phenylalanine methyl ester in said aqueous solution is about 2 wt. % or more.

14. The crystalline L-alpha-aspartyl-L-phenylalanine methyl ester product of claim 6, wherein the initial concentration of L-alpha-aspartyl-L-phenylalanine methyl ester in said aqueous solution is about 2 wt. % or more.

* * * * *